United States Patent [19]
Nashner

[11] Patent Number: 5,980,429
[45] Date of Patent: Nov. 9, 1999

[54] SYSTEM AND METHOD FOR MONITORING TRAINING PROGRAMS

[75] Inventor: Lewis M. Nashner, Lake Oswego, Oreg.

[73] Assignee: NeuroCom International, Inc., Clackamas, Oreg.

[21] Appl. No.: 09/041,877

[22] Filed: Mar. 12, 1998

Related U.S. Application Data

[60] Provisional application No. 60/040,435, Mar. 12, 1997.

[51] Int. Cl.$^6$ .................................................... A61B 5/103
[52] U.S. Cl. ............................... 482/8; 434/247; 600/595
[58] Field of Search .................................... 600/587, 595, 600/300; 482/1–9, 900–902; 434/247–258; 601/25; 73/379.01–379.09

[56] References Cited

U.S. PATENT DOCUMENTS

| | | | |
|---|---|---|---|
| 5,435,320 | 7/1995 | Seitz | 600/595 |
| 5,830,158 | 2/1998 | Zanakis | 600/595 |
| 5,868,578 | 2/1999 | Baum | 434/247 |

*Primary Examiner*—Glenn E. Richman
*Attorney, Agent, or Firm*—Bromberg & Sunstein LLP

[57] ABSTRACT

A system and method for monitoring training programs prescribed to benefit a subject. A training program prescriber may evaluate training effectiveness from a separate location from where a subject performs training tasks. Accuracy of actual task performances is measured and is compared with quality-benchmark data. The number of tasks actually performed is recorded and is compared with quantity-benchmark data. Benchmark-data may be obtained from previous subject performances or from performance by a defined reference population. Categorized results are calculated and assessments regarding program difficulty and motivation of the subject may be formulated. Compliance with expected program goals is analyzed and monitored.

11 Claims, 2 Drawing Sheets

SYSTEM AND METHOD FOR MONITORING TRAINING PROGRAMS

The present application claims priority from U.S. provisional application Ser. No. 060/040,435 filed on Mar. 12, 1997, which is incorporated herein by reference.

FIELD OF THE INVENTION

The invention relates to the monitoring of prescribed training programs to improve their cost-effectiveness and maintain quality control.

BACKGROUND ART

A major factor influencing the cost of skill training is the required level of supervision by a skilled practitioner. This is particularly crucial in today's health care environment in which more efficient use of medical resources is demanded. Allocating a portion of a subject's training to lower paid, less skilled assistants or having a subject train at home without professional supervision significantly reduces the labor costs. These reduced cost training programs increase the risk of inferior training outcomes because the insufficiently supervised trainee is more likely to perform tasks incorrectly, continue doing tasks which are either too simple or too difficult, or perform at a low level of intensity and motivation.

A second major factor particularly influencing the cost effectiveness of physical rehabilitation and athletic skill training is the motivation of the trainee to acquire the new skills required to enhance performance. A minority of individuals impaired either by injury or disease may have secondary reasons for slowing their recovery. For example, a worker receiving disability payments for a job related injury may prefer to remain on disability rather than have the injury rehabilitated only to return to an unsatisfying job. Similarly, an individual injured in a motor vehicle accident might be motivated to remain impaired in the hopes of winning a financial settlement. Such medical cases frequently occur in conjunction with legal actions in which a judge or jury are forced to make determinations of disability. Objective information related to a trainee's motivation to recover would be valuable in reaching these medical-legal judgments.

A third major factor particularly influencing the cost effectiveness of physical rehabilitation, but not limited to this type of program, is the quality of management. This is especially important in the realm of larger multi-facility corporate providers of training, operating with numerous practitioners. Traditionally, physical rehabilitation has been a clinical "art" in which the individual practitioner has a substantial degree of independence in determining the specific tasks used in treatment. Issues which must be addressed by quality management include: (1) Are individual practitioners adhering to the corporate standard methods used to treat specific physical disorders? (2) Are individual practitioners and patients working at the appropriate levels of motivation? (3) Are patients being adequately challenged during training to produce the best outcome in the shortest possible time? Objective information relative to the motivation, quantity, and quality of exercise tasks performed by patients would be valuable for the individuals responsible for managing the clinical program.

The challenge confronted by health care providers is to extend services to a broader population of individuals while minimizing the escalation of costs. To achieve this goal, providers must deliver their services in as cost-effective manner as possible and must concentrate services where they are likely to effect the greatest benefit. To deliver services efficiently, health care providers must select the most effective treatment approaches and predict the likely outcome of the selected approaches relative to the associated costs. For example, the demand for efficient physical rehabilitation services has become especially strong, because demand continues to increase rapidly in proportion to the growing numbers of elderly citizens.

A form of service now being implemented by providers is one which is home-based wherein a subject performs a substantial portion of prescribed training exercises at home rather than in a professionally supervised clinical environment. Rehabilitation training performed at clinics tends to be supervised by less skilled clinical aids and assistants rather than by professionally trained physicians and physical therapists. Both home-based and reduced cost clinically based approaches substantially reduce the personnel costs associated with rehabilitation training compared to the cost of services provided by professionally trained personnel. More responsibility is placed on patient motivation to perform the prescribed training exercises. When training exercises are performed in the absence of a professionally trained clinician, there is a substantially greater risk that the patient will be poorly motivated to perform at an optimal level of intensity, will continue to perform simpler, less challenging exercises when they are no longer needed, and will perform exercises incorrectly. All of these factors substantially reduce the efficacy of the rehabilitation training.

Motivation is a particularly critical factor for patients receiving physical rehabilitation for injuries sustained on the job or as a result of an accident. Many such patients are medical-legal cases for which there are potential monetary incentives for delaying recovery. The patient injured on the job may be entitled to compensation payments so long as the injury severity prevents return to work. In the case of motor vehicle and other accidents, liability payments are likely to be higher for more severe and sustained injuries. Methods and devices providing an objective evaluation of patient motivation during physical rehabilitation would be valuable not only in speeding recovery but also in exposing those patients who are poorly motivated to recover.

Although the research described below is undoubtedly applicable to a variety of training scenarios, the literature cited is taken from the current art of physical rehabilitation and athletic training. Selection of training exercises likely to yield the best outcome is typically based on information related to the trainee's medical diagnosis, results of functional performance assessments, and the trainee's goals for improvement. The functional performance assessment may employ either one or a combination of objective machine based and subjective observationally based methods. The current clinical literature suggests that information related to diagnosis and functional performance contribute useful information to the processes of selecting the most effective training tasks and predicting the progress and outcome of performing said tasks.

It is generally accepted in the scientific literature pertaining to motor learning and skill acquisition that the number and the intensity of practice repetitions of an exercise and the motivation of the individual performing the exercise substantially influence the speed at which a new skill is acquired and the eventual level of proficiency attained (see for example: Schmidt, Motor Control and Learning, A Behavioral Emphasis. Champaign, Ill., Human Kinetics Publishers, 1988). Thus, individuals who exert higher levels of effort performing a training exercise as well as those who spend more time performing the exercise are likely to reach higher levels of proficiency more quickly compared to individuals expending less effort and time. This finding is easily extendable to many forms of training.

Another generally accepted principle in the scientific literature pertaining to motor learning and skill acquisition is that effective skill acquisition requires matching the exercise difficulty with the individual's performance capabilities relative to the exercise (see for example: Winstein, et al, Standing balance training: effect on balance and locomotion in hemiplegic adults, Archives of Physical Medicine and Rehabilitation, 70, 1989). If the exercise is too difficult relative to a trainee's performance capabilities, the trainee's performance is poor, little if any reinforcing feedback is received, and relatively less is acquired in the way of new skill. At the other extreme, if the training task is simple relative to the performance capabilities of the trainee, the accuracy of the trainee's performance will be very high, but the trainee will lack sufficient challenge to acquire additional skill. Research studies indicate that skill acquisition is most effective when the exercise challenge enables the trainee to correctly perform approximately one-half of his attempts. The above principles of skill acquisition are understood in such diverse fields as sports training, musical performance, dance, high performance aircraft piloting, to name a few. The clinical literature suggests that these same principles of skill acquisition pertain to patients attempting to re-learn or improve skills lost through disease and physical injury (see for example: Rose, Older Adults Assessing and Treating Multiple Dimensions of Balance, Rehab Management, December/January 1997).

A well accepted principle of education is that a trainee striving to achieve a clearly defined, objective goal while receiving periodic objective feedback relative to his progress is the best motivated. Anecdotally, this principle is demonstrated by the intensity at which children and adults perform computer-based video games. Motivation is further enhanced when the trainee knows in advance that the supervising trainer will also be receiving periodic feedback regarding progress relative to the prescribed goal.

Apparatus and method for the assessment of and biofeedback training of movement coordination, strength, and speed skills are the subject of U.S. Pat. No. 5,476,103, issued Dec. 19, 1995 to Lewis M. Nashner and of U.S. Pat. No. 5,551,445, issued Sep. 3, 1996 to Lewis M. Nashner. In addition, the assessment of and biofeedback training of body coordination skills and ball-strike power and accuracy during athletic activities is the subject of U.S. Pat. No. 5,697,791 to Nashner, et al., issued Dec. 16, 1997. This art, as well as other related patent applications and other references cited in these patents, are incorporated herein by reference. The equipment and methodology disclosed in preferred embodiments provide examples of building blocks upon which the aforementioned goals of this disclosure might be realized.

SUMMARY OF THE INVENTION

The invention provides a system for monitoring the effectiveness of a training program. A training program prescriber may evaluate the suitability of an individualized program from a separate location from where a subject performs prescribed training tasks. The prescribed program includes at least one task to be performed a plurality of times during a defined interval of time.

A specific embodiment provides that data obtained using quality-measuring means designed to measure the accuracy of actual task performances is compared with quality-benchmark data. At least one quality result obtained from such a comparison is calculated and displayed. Such results may suggest desirable changes to a training program for increased effectiveness while minimizing required on-site intervention by skilled professionals.

A preferred embodiment provides that data is also obtained using quantity-measuring means, is compared with quantity-benchmark data and at least one quantity result is calculated and displayed. The results may be further categorized and assessments regarding the difficulty of the program and the motivation of the subject may be obtained.

In another preferred embodiment, information is provided to the subject regarding goals of the training and how well the goals are being achieved. Insight regarding the motivation of the subject may be made as well as the potential need for re-instruction.

In another embodiment, a method for monitoring training program effectiveness including the steps of measuring, comparing, and calculating quality and quantity results is provided. The comparisons may be made between actual performance and previous performance by the same subject or between actual performance and performance by a defined reference population. Compliance with expected program goals is analyzed and monitored. Results are categorized and conclusions are drawn as to program effectiveness.

DESCRIPTION OF SPECIFIC EMBODIMENTS

Figure 1:
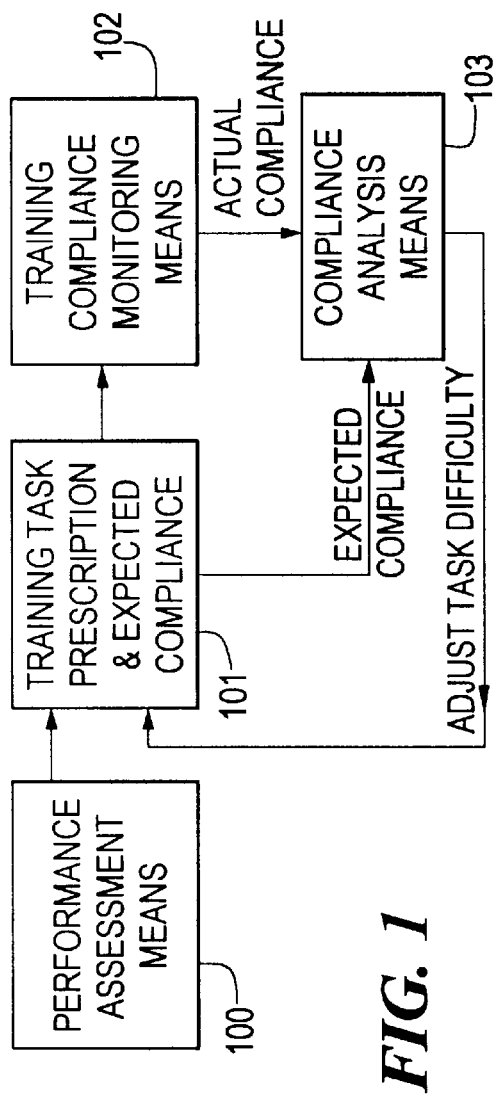
FIG. 1 is a flow chart describing how a prescriber may create and revise an individualized training program.

FIG. 1 illustrates a basic system which a prescriber may use when developing an individualized training program. The prescriber first determines the initial conditions. An assessment 100 of the present capabilities of the subject is made. This involves determining the current skill level of the individual and deciding the overall performance goals to be achieved within the scope and duration of training. It may be advantageous to record one or more initial quantity and quality performance measures upon which the subject will build during the program. The specific training program may then be created 101 consisting of one or more tasks defining the expected performance in terms of quality and quantity of executed tasks. Progress toward performance goals is, then, actively monitored 102 by the prescriber by comparing actual task performance with quality and quantity expectations 103. This requires a significant time and monetary commitment by both a professional prescriber and the subject.

Figure 2:
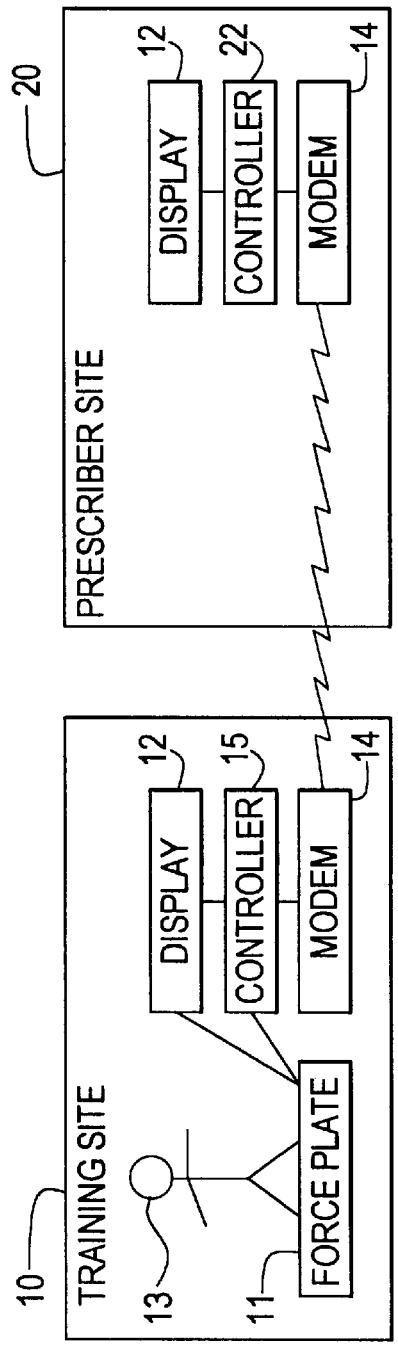
FIG. 2 schematically illustrates an example of a monitoring system in accordance with an embodiment of the invention.

In accordance with an embodiment of the invention, compliance monitoring of a training program may be remotely accomplished by a prescriber. FIG. 2 illustrates a specific example of a monitoring system. Training site 10 may be the home of a subject 13 or other location at some distance from a prescriber site 20. For example, prescriber site 20 may be a professional office, a health care facility or an educational facility. Tasks are performed by the subject 13 at training site 10, while monitoring is occurring at prescriber site 20. A quality and quantity-measuring device 11 (in this example, a force plate) is in communication with subject 13 during task performance. Data communication between quality and quantity-measuring device 11 and display unit 21 may be established by use of one or more modems 14 or other effective linkages. In accordance with a preferred embodiment, measurements made using device 11 serve to quantify, for example, the accuracy of task performance by the subject 13 as well as to count the number of tasks performed over a defined time period. A comparator or other means effective in comparing data (not shown) compares the measurement and benchmark inputs and is capable of providing these inputs in a format suitable for further calculation. The comparison means may be located at either site 10 or at site 20. It may be free-standing and in data communication with device 11 and unit 21 or may be an integral component of either device 11 or of unit 21. Quality-benchmark data and quantity-benchmark data may be entered and stored in the comparison means or input to the comparison means from a library (not shown) with suitable data communication linkage. Resultant data is further analyzed at site 20 yielding at least one result. Suitable analysis means (shown as controller 22) may be free-standing and in data communication with unit 21 or may be an integral component of unit 21. Results are displayed to the prescriber from display unit 21. In accordance with a preferred embodiment, a task-display unit 12, in data communication with device 11, is provided at site 10. The task-display unit 12 provides information to the subject 13 regarding tasks being performed as part of the training program. Suitable analysis means (shown as controller 15) may also be provided, in data communication with task-display unit 12.

In another embodiment of the invention, displayed results are further categorized to provide feedback to the prescriber regarding the effectiveness of the individualized training program. Information related to the subject's compliance is compared to information related to the expected performance and the results of the comparison used to help make determinations of training effectiveness based on one or more of the following: (a) the subject's level of motivation and (b) the level of training task difficulty relative to the subject's performance capabilities.

In a preferred embodiment of the invention, the subject's motivation and the appropriateness of the prescribed training program is determined based on a comparison of the expected training performance and the subject's actual compliance, with the subject serving as his or her own control. This method includes the following steps: (1) the subject is assessed and quantities related to initial performance capabilities are documented, (2) a training program is prescribed and expected compliance defined relative to the subject's performance capabilities determined in step (1), (3) one or more measurements related to the quantity and accuracy of actual compliance are recorded during execution of the training tasks, and (4) subject motivation, appropriateness of task challenge, and potential for improvement are determined based on algorithms for combining the expected and compliance information as described in Table 1.

TABLE 1

| ACCURACY OF PERFORMANCE RELATIVE TO EXPECTED | QUANTITY OF TRAINING TASKS PERFORMED RELATIVE TO EXPECTED | | |
|---|---|---|---|
| | BELOW EXP. | EQUAL EXP. | ABOVE. EXP. |
| BELOW EXP. | Unmotivated | Possibly Unmotivated | Re-Instruct |
| EQUAL EXP. | Possibly Unmotivated | Appropriate | Possibly Unchallenged |
| ABOVE EXP. | Re-Instruct | Possibly Unchallenged | Unchallenged |

The following determinations regarding the effectiveness of training are made in accordance with Table 1:

(1) When both the accuracy and the quantity of a subject's actual compliance with the training tasks are substantially lower than the expected compliance, the subject's performance is inconsistent, and the subject is unmotivated to exert sufficient effort during training. When a subject's effort is insufficient, the training program is unlikely to achieve the full potential for improvement. In these cases, the subject's motivation should be improved.

(2) When both the accuracy and quantity of a subject's compliance with the training exercises are substantially similar to the expected compliance, the subject's performance is consistent, the subject's motivation is sufficient, and the training program is likely to achieve the full potential for improvement.

(3) When both the accuracy and quantity of the subject's compliance is substantially higher than the expected compliance, the subject's performance is inconsistent, the subject is insufficiently challenged, and the exercise program is unlikely to achieve the full potential for improvement. In these cases, the difficulty of the training program should be increased.

(4) When the accuracy of a subject's compliance with the training task is lower than expected compliance and the quantity of tasks performed as similar to the expected, or the accuracy is similar to expected compliance but the quantity is lower than the expected, the subject's performance is partially inconsistent, the subject may be unmotivated and exerting less than sufficient effort, and the exercise program may not achieve the full potential for improvement.

(5) When the accuracy of a subject's compliance with the prescribed exercise program is similar to the expected compliance but the quantity of exercises performed is higher than the expected, or the quantity of exercises performed is similar to the expected compliance but the accuracy is higher than the expected, the subject's performance is partially inconsistent, the subject is possibly insufficiently challenged, and the exercise program may not achieve the full potential for improvement.

(6) When the task accuracy and quantity indicators are highly inconsistent with one another, specifically one indicator is higher than the expected compliance and the other is lower than the expected, the subject is not complying with the goals of the task. In these instances, the subject should be re-instructed in the training task goals and the training repeated.

In another embodiment of the invention, the subject's motivation and the appropriateness of the selected training tasks are determined by comparing the subject's initial functional performance assessment data with performance, and training compliance data derived from a reference population of individuals. This method includes the following steps: (1) an initial evaluation of the training candidate's deficit from a norm is made, the subject's performance capabilities relative to the performance goals are assessed, and one or more quantities related to the subject's performance capabilities are recorded, (2) a training task is selected and expected compliance defined, based on the compliance achieved by the reference population and, (3) one or more quantities related to the quantity and accuracy of the subject's actual compliance with the training are recorded, and (4) subject motivation and appropriateness of training tasks are determined based on Table 2 shown below.

TABLE 2

| ACCURACY OF PERFORMANCE RELATIVE TO REFERENCE POPULATION | QUANTITY OF TRAINING TASKS PERFORMED RELATIVE TO REFERENCE POPULATION | | |
| --- | --- | --- | --- |
| | BELOW REF. | EQUAL REF. | ABOVE. REF. |
| BELOW REF. | Too Difficult | Possibly Too Difficult | Re-Instruct |
| EQUAL REF. | Possibly Too Difficult | Appropriate | Possibly Too Easy |
| ABOVE REF. | Re-Instruct | Possibly Too Easy | Too Easy |

The following decisions regarding training are made in accordance with Table 2:

(1) When both the accuracy and the quantity of a subject's actual compliance with the training task are substantially lower than the compliance of the reference population, the selected training tasks are too difficult for the trainee. When a training task is too difficult, the exercise program is unlikely to achieve the full potential for improvement. In these cases, the difficulty of the training program should be reduced.

(2) When both the accuracy and quantity of a subject's compliance are equal to that achieved by the reference population, the training task difficulty is appropriate, and the training program is likely to achieve the full potential for improvement.

(3) When both the accuracy and quantity of the subject's compliance is substantially higher than that achieved by the reference population, the selected training exercise is too easy for the subject's, and the training program is unlikely to achieve the full potential for improvement. In these cases, the difficulty of the training program should be increased.

(4) When the accuracy of a subject's compliance with the training task is lower than that achieved by the reference population but the quantity of exercises performed is equal, or the accuracy of a subject's compliance with the training task is equal to that achieved by the reference population but the quantity of exercises performed is lower, the training tasks may possibly be too difficult for the trainee, and the exercise program may not achieve the full potential for improvement.

(5) When the accuracy of a subject's compliance with the training task is equal to that achieved by the reference population but the quantity of tasks performed is higher, or the quantity of tasks performed is equal to that achieved by the reference population but the accuracy is higher, the tasks may possibly be to easy for the subject, and the exercise program may not achieve the full potential for improvement.

(6) When the task accuracy and quantity indicators are highly inconsistent relative to the reference population, specifically one indicator is higher than the reference and the other is lower, the subject is not complying with the goals of the task. In these instances, the subject should be re-instructed in the training task goals and the training repeated.

The following examples relate to physical rehabilitation and physical coordination. The system and method will be described in terms of physical rehabilitation and physical coordination without limitation. Any other training programs are included within the scope of the invention as described herein and as claimed in any appended claims.

The New Balance Master version 6.0 produced by NeuroCom International, Inc. of Clackamas, Oreg. provides assessment information in a form that can be used by a practitioner skilled in the art of physical rehabilitation for prescribing an exercise program and for defining the expected compliance with the program. An upgraded version will further provide a menu of standardized training tasks which can be used by a skilled practitioner in physical rehabilitation to implement a training program and monitor a patient's compliance with the prescribed program.

The New Balance Master includes a functional performance assessment means for objectively assessing a patient's ability to perform balance and mobility tasks representative of daily living, an analysis means for displaying the patient's performance on the assessment means and for comparing the patient's performance to that of an age-matched normal reference population, a training means comprised of a menu of structured exercise tasks subdivided by activity type and level of difficulty, and an additional assessment means for documenting the patient's compliance with exercises performed with the training means.

Figure 3:
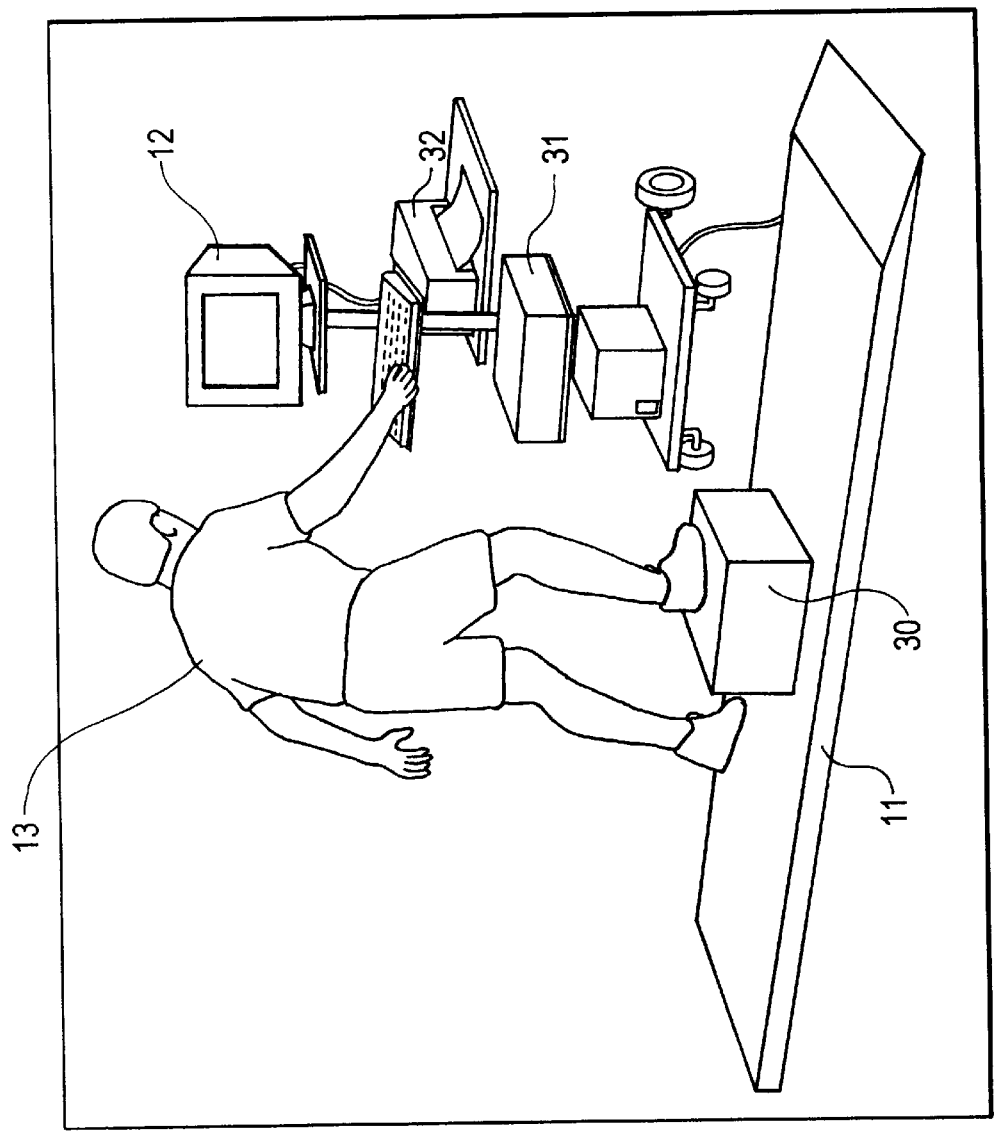
FIG. 3 shows a system which may be used by a practitioner skilled in the art of physical rehabilitation for prescribing an exercise program and for defining the expected compliance with the program, according to a preferred embodiment of the invention.

The New Balance Master is comprised of the following components illustrated in FIG. 3: (1) The forceplate 11 measures variables of force related to an individual's performance during prescribed seated, standing, and walking assessment and exercise training tasks. (2) Tools 30 are available for placement on the forceplate to enable performance of various additional assessment and exercise training tasks such as step up/down and sit to stand. (3) The computer 31 receives force information derived from the forceplate, processes forceplate information to provide measures related to the individual's performance and real-time biofeedback displays to be used during the training exercises, and generates task instructions and goals to be used during the training exercises. (4) The visual display 12 receives information from the computer and displays training task exercise instructions and goals and displays the real-time biofeedback information. (5) The printer 32 receives information from the computer and generates hard-copy reports related to the results of assessment and compliance with training.

The New Balance Master assessment protocols are designed to assess the performance capabilities of the patient on a variety of specific types of balance and mobility tasks. Results of performing each assessment task are is analyzed and displayed in a comprehensive report including graphical summaries of average scores, coefficients of variation, and left-right percentage difference scores where appropriate. Left/Right difference scores are presented for those measures which differentiate between performance of the left and right lower extremity. Each comprehensive report also includes the capability of comparing an individual patient's scores to those of a reference population of individuals. Typically, the reference population will consist of a group of normal individuals age-matched to the patient or a group of patients with similar diagnoses.

The following comprehensive assessment reports provide objective information to identify the type and severity of balance and mobility problem areas so that a practitioner skilled in the art of physical rehabilitation can prescribe an exercise program which targets identified problem areas at an appropriate level of difficulty.

1. Sit To Stand: The patient assumes a comfortable seated position on a backless stool with the feet placed in standardized positions. The patient rises on command to a standing position as quickly and as comfortably as possible and to maintain the erect position for 5 seconds. The task is repeated three times. The difficulty of the task can be adjusted by modifying the height of the stool. Performance measures include the following:

(1) Weight Transfer Time is the time in seconds required to voluntarily shift the COG forward from the seat to the base of foot support.

(2) Rising Index documents the maximum vertical force exerted by the legs during the rising phase. This force is expressed as a percentage of the patient's body weight.

(3) COG Sway documents control of the COG over the base of support during the rising phase of the maneuver and for 5 seconds thereafter. Sway is expressed as mean velocity of COG sway in degrees per second.

2. Walk: The patient stands at one end of the forceplate and on command initiates gait to walk from one end of the forceplate to the other as quickly and comfortably as possible, and then terminates gait at the other end of the forceplate. The task is repeated three times. Task difficulty is increased by requiring tandem heel to toe stepping. The following performance measures are calculated:

(1) Stride Width is the lateral distance in inches between successive steps.

(2) Stride Length is the longitudinal distance in inches between successive steps.

(3) Speed is the velocity in feet per second of the forward progression.

(4) End Sway is the mean velocity in degrees per second of the antero-posterior (AP) component of COG sway after the patient terminates walking.

3. Step/Quick Turn: The patient takes two steps forward, executes a 180 degree in-place turn as quickly and comfortably as possible, and then resumes walking in the opposite direction. The maneuver is repeated three times with the patient turning to the right and three times turning to the left. The Comprehensive Report includes the following two performance measures for each turn direction:

(1) Turn Time quantifies the number of seconds required for the individual to execute the 180 degree in-place turn. Turn time begins when forward progression is arrested and ends when progression in the opposite direction is initiated.

(2) Turn Sway quantifies the postural stability of the individual during the turn time defined above. Turn Sway is expressed as the average COG sway path length in degrees.

4. Step Up/Over: The individual stands in front of a raised platform, steps onto the platform with the leading leg, swings the opposing leg over the platform and down onto the surface on the opposite side. The maneuver is performed as quickly and as comfortably as possible and repeated three times each with left and right lower extremities. The following performance measures are calculated for each extremity:

(1) Lift-Up Index quantifies the maximum lifting (concentric) force exerted by the leading leg and is expressed as a percentage of the patient's weight.

(2) Movement Time quantifies the time required to complete the maneuver, beginning with the initial weight shift to the non-stepping (lagging) leg and ending with impact of the lagging leg onto the surface. Time is measured in seconds.

(3) Impact Index quantifies the maximum vertical impact force as the lagging leg lands on the surface. The force of impact is expressed as a percentage of the patient's weight.

5. Forward Lunge: The patient lunges forward as far, quickly, as is comfortably possible three times with each lower extremity. During each lunge, the patient reaches to the maximum distance and, with a smooth continuous movement, then pushes back to the starting position. The report includes the following performance measures for each extremity:

(1) Distance is the lunge length expressed as a percentage of the patient's height.

(2) Impact Index is the maximum vertical force exerted by the stepping leg onto the surface during the landing, expressed as a percentage of the patient's body weight.

(3) Contact Time is the duration in seconds of surface contact with the lunging leg in the forward (or lateral) position.

(4) Force Impulse is a measure of the total work performed by the lunging leg during the landing and thrust phases of the movement. Force impulse is expressed in units of % body weight (force) multiplied by the time the force is exerted in seconds.

6. Weight Bearing/Squat: To accommodate the differing functional levels of patients, the Weight Bearing/Squat is performed with weight bearing only in the fully erect position, fully erect, 30, and 60 degrees of knee flexion, or fully erect, 30, 60, and 90 degrees of knee flexion.

7. Bilateral (Unilateral) Stance: The patient assumes a quiet standing position and is instructed to maintain the position as still as is comfortably possible. Each condition is repeated three times. Bilateral stance (Level I and II) trials last 20-seconds each, while the Level III trials last 10 seconds.

COG Sway is the mean sway velocity in degrees per second.

Composite Sway is the mean sway velocity averaged over the six trials.

COG Alignment is the position of the center of gravity at the start of each trial, expressed as displacement from center in the forward-backward and lateral directions.

8. Limits Of Stability: The patient stands with feet in standardized positions, views a cursor display of their COG position, and orients himself so that the COG cursor coincides with a target representing the center of the LOS area. A second target is then placed a predetermined distance from center relative to the LOS boundary. The patient moves the COG cursor on command as quickly and as accurately as possible to the perimeter target and to hold the perimeter position for five seconds. The task is repeated with a total of eight perimeter targets, representing the four cardinal directions (forward, backward, left, right) and the four diagonal directions. Results of the eight target movements are combined into the four cardinal directions by a weighted averaging of the forward-backward and left-right components of the diagonal movement scores into the relevant cardinal direction scores. The report shows the following measures for forward, backward, right, and left target movements:

(1) Reaction Time is the time in seconds between the command to move and the point at which the patient first initiates movement.

(2) Movement Velocity is the average speed of movement in degrees per second measured between the time the patient reaches 5% of the End Point distance until 95% of the End Point distance is achieved.

(3) End Point Excursion is the distance reached upon completion of the first movement to the target. Distance is expressed as a percentage of the theoretical maximum LOS distance. The first movement is completed when progress towards the target ceases.

(4) Maximum Excursion is the maximum distance achieved during the trial. The maximum excursion may be larger than the End Point excursion if the patient initiates additional movements towards the target following the termination of the first.

(5) Directional Control is the off-axis (left and/or right of the straight line path to the End Point) distance moved by the patient compared to the on-axis distance moved (the straight line path) to the End Point. Direction control is calculated by subtracting the off-axis distance from the on-axis distance, and expressing the difference as a percentage of the actual on-axis distance. A Direction Control score of 100% indicates a perfect straight line movement from the center to the End Point defined above, while lower percentages indicate larger off-axis movements.

9. Rhythmic Weight Shift: The patient stands in-place with feet in standard positions on the forceplate. The patient views a cursor display of their COG position and is instructed to move rhythmically such that the COG cursor moves back and forth the full distance between two boundaries spaced in opposite directions from center and at 50% of the distance to the LOS perimeter. The required rhythm of the back and forth movement is demonstrated to the patient by a pacing target. The patient performs the task either with rhythmic antero-posterior movements or lateral movements between boundaries placed either to the front and back or to the left and right of the center position, respectively.

To accommodate the differing functional levels of patients, the Rhythmic Weight Shift assessment is included in all three levels of difficulty:

(1) Level I (easy) with the pacing targets moving slowly at one cycle every three seconds, (2) Level II (moderate) with the pacing target moving at one cycle every two seconds, and (3) Level III (challenging) with the pacing target moving rapidly at one cycle per second. The Rhythmic Weight Shift report includes the following measures:

(1) On-Axis Velocity is the average speed in degrees per second of the rhythmic movement along the specified movement direction.

(2) Direction Control is the average velocity of on-axis motion expressed as a percentage of the total (on-axis and off-axis velocity) motion.

The new Balance Master training protocols are designed to provide the treating practitioner with a menu of training exercises which are grouped by task type and difficulty level. Because the assessment and training protocols are organized into the same task groups, the assessment results can be readily used by a practitioner skilled in the art of physical rehabilitation or athletic training to prescribe training tasks of the type and difficulty levels which are likely to achieve functional improvements in performance.

1. Seated Activities: Seated exercises begin at the lowest levels with control of trunk alignment over the base of support. Intermediate levels exercise the patient's ability to perform weight shifts to specified points within the base of support and to maintain alignment on compliant and movable seated surfaces. The highest levels of seated exercise include trunk control functions necessary for transition from seated to standing activities.

2. Weight Shifting Activities: Weight shifting exercises are performed in freely standing positions and emphasize the maintenance of body alignment and active center of gravity control to all locations within the limits of stability area. At the lowest levels of exercise alignment and movement activities are performed on stable, firm surfaces between locations well within the limits of stability. More challenging weight shifting exercises are performed on compliant foam rubber and moving rocker board surfaces, and patients are required to move to locations at the outermost boundaries of the limits of stability. All levels of weight shift training allow the user to emphasize forward, backward, left, or right movement directions.

3. Lower Extremity Closed Chain Activities: Lower extremity closed chain activities are performed in freely standing and weight bearing positions and emphasize the weight control, strength, flexibility, and motor control component functions. Activities can be modified to emphasize the left or right extremity and to focus on the ankle, knee, hip, or lower back of the designated side. Lower levels exercise the targeted joint while the patient maintains less than full 100% weight on the involved leg. Higher levels use steps, wedges, and lunge movements to modify the range of joint motion during full weight bearing exercises. Tasks involving controlled COG movements over the base of support at all levels of training exercise lower extremity proprioception and motor control. The challenge is increased at the higher levels by increasing the movement distances and by performing the movements on foam rubber, wedge, and rocker board surfaces.

4. Mobility Activities: Mobility activities involve freely moving sit to stand, stepping, turning, and climbing tasks performed over the full extent of the forceplate surface. The tasks emphasize gait stability, step placement and planning, maneuvering over obstacles, and changes in gait direction. The lowest levels of exercise emphasize preparation for and transitions between sitting and standing. Intermediate levels emphasize weight shifts and step initiation, while the highest levels involve narrow based gaits, obstacles, turns, and complex step placement patterns.

Training exercises within each of the above task groups are divided into five levels of difficulty designed to address the evolving needs of the patient over the course of recovery. Level I training exercises are designed for the earliest phases of recovery when assessment results indicate that the patient performed well below levels of the reference population. At the other extreme, Level V exercises are designed for maximizing the training challenge of the highest level patients and skilled athletes when assessment results indicate that the patient performed well above levels of the reference population. Training Levels II through IV are designed to progressively increase the challenge in graded steps between the earliest phases of recovery and the maximum challenge.

Each training sequence provides the following compliance information:

1. Training Quantity: The Training Quantity portion of the patient's compliance information file informs the clinician relative to the date(s), exercise task type(s), exercise task difficulty level(s) and repetition of each task performed.

2. Training Quality: Depending on the level of challenge selected, a typical exercise task contains one hundred or more individual movement repetitions. For each task performed, the Training Quality portion of the report compares the total number of movement repetitions attempted by the patient to the number of repetitions in which the patient successfully reached the appropriate target goal. For purposes of compliance documentation, a repetition is deemed successfully completed when the patient moves the COG cursor into the designated target zone within the time allotted for the individual movement.

3. Training Report: A summary report is generated for a training session consisting of one or more exercise tasks. The graphic portion of the report illustrates the target configuration and COG cursor path for each exercise task. A complete session typically contains up to seven exercise tasks, depending on the difficulty level. The numerical data associated with each exercise includes:

(1) Exercise Task Duration: The duration of the exercise in seconds.

(2) Successful Target Repetitions: The number of target repetitions successfully completed.

(3) Attempted Target Repetitions: The number of target repetitions attempted.

Included in the New Balance Master assessment is the capability to compare the performance results of the individual patient to that of a reference population of individuals. The graphic presentations of each comprehensive report, areas falling outside the performance range achieved by 95% of the reference population are shaded, whereas areas falling within the 95% range are not shaded. By observing the location of the patient's results on the graph relative to the shaded and unshaded areas, the practitioner can readily determine the performance capabilities of the patient relative to those of the reference population.

Although the invention has been described with reference to several preferred embodiments, it will be understood by one of ordinary skill in the art that various modifications can be made without departing from the spirit and the scope of the invention, as set forth in the claims hereinbelow.

I claim:

1. A system for monitoring the effectiveness of a training program prescribed to a subject by a prescriber, the training program including at least one task to be performed a plurality of times during a defined time period by the subject, the system comprising:

quality-measuring means, located at a first site, for measuring the accuracy of the performances of the at least one task and providing quality-measurement data;

comparison means for comparing the quality-measurement data with quality-benchmark data; and analysis-display means, located at a second site, for displaying to the prescriber at least one quality result calculated from at least one comparison between the quality-measurement data and the quality-benchmark data.

2. A system as in claim 1, further comprising:

quantity-measuring means, located at the first site, for measuring the number of performances of the at least one task and providing quantity-measurement data;

comparison means for comparing the quantity-measurement data with quantity-benchmark data; and analysis-display means, located at a second site, for displaying to the prescriber at least one quantity result calculated from at least one comparison between the quantity-measurement data and the quantity-benchmark data.

3. A system for monitoring the effectiveness of a training program prescribed to a subject by a prescriber, the training program including at least one task to be performed a plurality of times during a defined time period by the subject, the system comprising:

task-display means, located at a first site, for displaying at least one goal of the at least one task to the subject;

quantity-measuring means, located at the first site, for measuring the number of performances of the at least one task and providing quantity-measurement data;

quality-measuring means, located at the first site, for measuring the accuracy of the performances of the at least one task and providing quality-measurement data;

comparison means for comparing the quantity-measurement data with quantity-benchmark data and for comparing the quality-measurement data with quality-benchmark data; and analysis-display means, located at a second site, for displaying to the prescriber at least one quantity result calculated from at least one comparison between the quantity-measurement data and the quantity-benchmark data and for displaying at least one quality result calculated from at least one comparison between the quality-measurement data and the quality-benchmark data.

4. A system according to claim 3, wherein the analysis-display means further includes:

means for categorizing the at least one quantity result into one of a plurality of categories; and means for categorizing the at least one quality result into one of a plurality of categories.

5. A system according to claim 4, wherein:

the at least one quantity result is categorized in a first quantity category when the quantity-measurement data is substantially below the quantity-benchmark data, the at least one quantity result is categorized in a second quantity category when the quantity-measurement data is substantially equivalent to the quantity-benchmark data, the at least one quantity result is categorized in a third quantity category when the quantity-measurement data is substantially above the quantity-benchmark data, the at least one quality result is categorized in a first quality category when the quality-measurement data is substantially below the quality-benchmark data, the at least one quality result is categorized in a second quality category when the quality-measurement data is substantially equivalent to the quality-benchmark data, and the at least one quality result is categorized in a third quality category when the quality-measurement data is substantially above the quality-benchmark data.

6. A system according to claim 5, wherein the quantity-benchmark data includes the expected number of times the subject is expected to perform the task, and wherein the quality-benchmark data includes the expected accuracy with which the subject is expected to perform the task.

7. A system according to claim 5, wherein the quantity-benchmark data and the quality-benchmark data are derived from a reference population.

8. A system according to claim 3, wherein the prescriber includes a group of trainers.

9. A system according to claim 3, wherein the prescriber includes a group of health care professionals.

10. A system according to claim 3, wherein the task-display means further comprises:

means for displaying to the subject at least one quantity result calculated from at least one comparison between the quantity-measurement data and the quantity-benchmark data and for displaying at least one quality result calculated from at least one comparison between the quality-measurement data and the quality-benchmark data.

11. A system for determining whether a prescribed training task is appropriately difficult relative to a subject's ability and whether best effort is being exerted by the subject to accomplish the training task, the system comprising:

(1) a device for measuring one or more quantities related to the subject's performance relative to one or more specified training tasks, (2) a device for displaying one or more goals to the subject relative to the one or more training tasks, (3) a device for displaying information to the subject related to performance relative to the one or more displayed task goals, (4) a device for calculating one or more quantities related to number of training tasks attempted and to accuracy of performance relative to the one or more task goals, and (5) a device for comparing quantities related to the number of training tasks attempted calculated by the device of element (4) and quantities related to the accuracy of performance calculated by the device of element (4), in accordance with a specified algorithm.

* * * * *